(12) United States Patent
Genty et al.

(10) Patent No.: US 10,117,838 B2
(45) Date of Patent: Nov. 6, 2018

(54) PHARMACEUTICAL COMPOSITION FOR THE PROLONGED RELEASE OF TRIMETAZIDINE

(71) Applicant: LES LABORATOIRES SERVIER, Suresnes (FR)

(72) Inventors: Patrick Genty, Orléans (FR); Christophe Hermelin, Chaingy (FR); Jean-Manuel Pean, Orléans (FR)

(73) Assignee: LES LABORATOIRES SERVIER, Suresnes (FR)

( * ) Notice: Subject to any disclaimer, the term of this patent is extended or adjusted under 35 U.S.C. 154(b) by 0 days.

(21) Appl. No.: 13/753,313

(22) Filed: Jan. 29, 2013

(65) Prior Publication Data
US 2013/0202710 A1 Aug. 8, 2013

(30) Foreign Application Priority Data
Feb. 3, 2012 (FR) ..................................... 12 00322

(51) Int. Cl.
*A61K 9/50* (2006.01)
*A61K 31/495* (2006.01)
*A61K 47/02* (2006.01)

(52) U.S. Cl.
CPC .......... *A61K 9/5047* (2013.01); *A61K 9/5078* (2013.01); *A61K 31/495* (2013.01); *A61K 47/02* (2013.01)

(58) Field of Classification Search
CPC .. A61K 31/495; A61K 9/5078; A61K 9/2027; A61K 9/2806; A61K 9/4808; A61K 9/5047
See application file for complete search history.

(56) References Cited

U.S. PATENT DOCUMENTS

| | | | | |
|---|---|---|---|---|
| 3,080,294 | A * | 3/1963 | Shepard ............... | A61K 9/5015 424/467 |
| 2009/0110728 | A1* | 4/2009 | Rastogi et al. ............... | 424/468 |
| 2011/0274751 | A1* | 11/2011 | Cifter et al. .................. | 424/465 |
| 2011/0300209 | A1* | 12/2011 | Surve et al. .................. | 424/452 |
| 2011/0311631 | A1* | 12/2011 | Baer et al. .................... | 424/486 |

FOREIGN PATENT DOCUMENTS

CN 102133195 A * 7/2011
WO WO 03043610 A2 * 5/2003

OTHER PUBLICATIONS

Detry et al (British Journal of Clinical Pharmacology, 1994, vol. 37, pp. 279-288).*
Sigma-Aldrich (Polyethylene glycol and polyethylene oxide, http://www.sigmaaldrich.com/materials-science/material-science-products.html?TablePage=20204110, 2015).*
Mindfully.org (Polyethylene Glycols (PEGs), http://www.mindfully.org/Plastic/Polymers/Polyethylene-Glycols-PEGs.htm, 2015).*
Takeshita et al (Toxicological Sciences, online Jul. 8, 2011, vol. 123, pp. 460-470).*
Chen, Wang, et al (CN 102133195 A, Jul. 2011, English translation from Espacenet on Jun. 14, 2017).*
Rowe, et al., Handbook of Pharmaceutical Excipients, Fifth Ed., 2006, pp. 545 and 551.

* cited by examiner

*Primary Examiner* — Mark V Stevens
(74) *Attorney, Agent, or Firm* — Hueschen and Sage

(57) ABSTRACT

Composition for the prolonged release of trimetazidine wherein the inner phase comprises trimetazidine and the outer layer comprises a retardant and an anti-agglomerant.

16 Claims, 5 Drawing Sheets

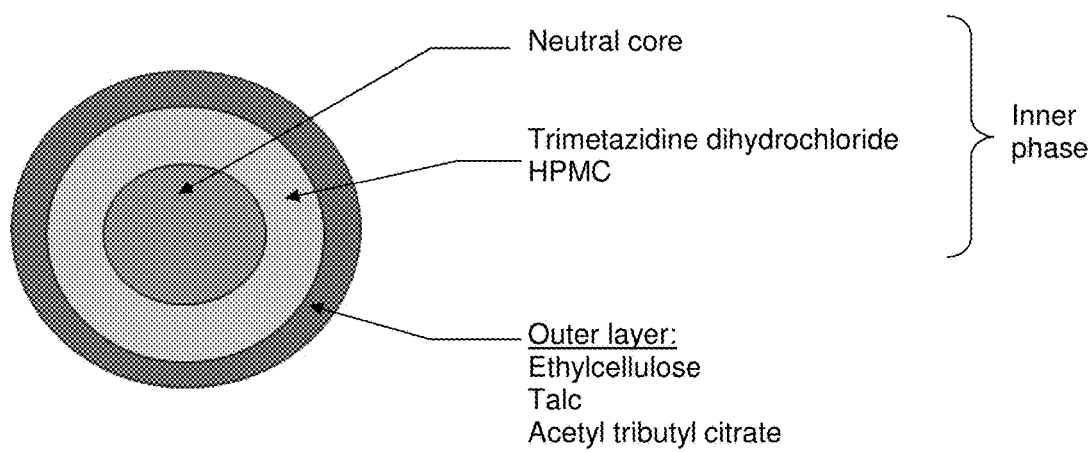
Figure 1: Structure and formulation of the pharmaceutical compositions

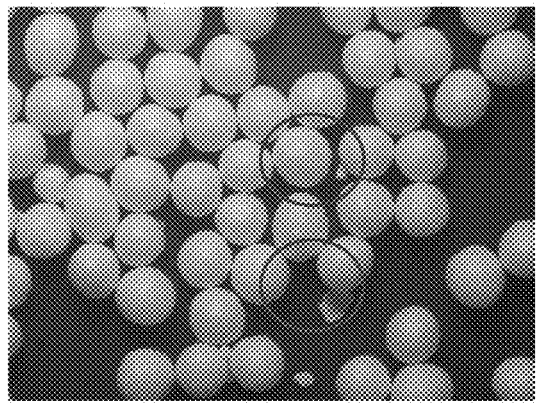
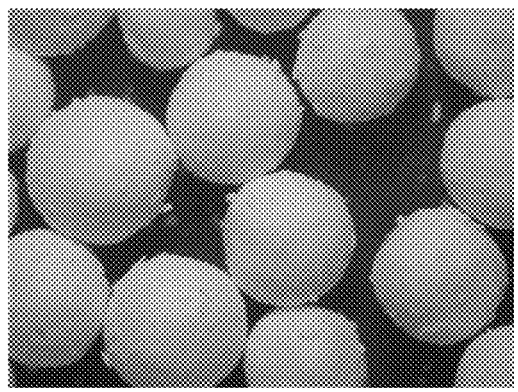
Figure 2: Comparative appearance of minigranules without anti-agglomerant (top) and with an excess of anti-agglomerant (bottom)

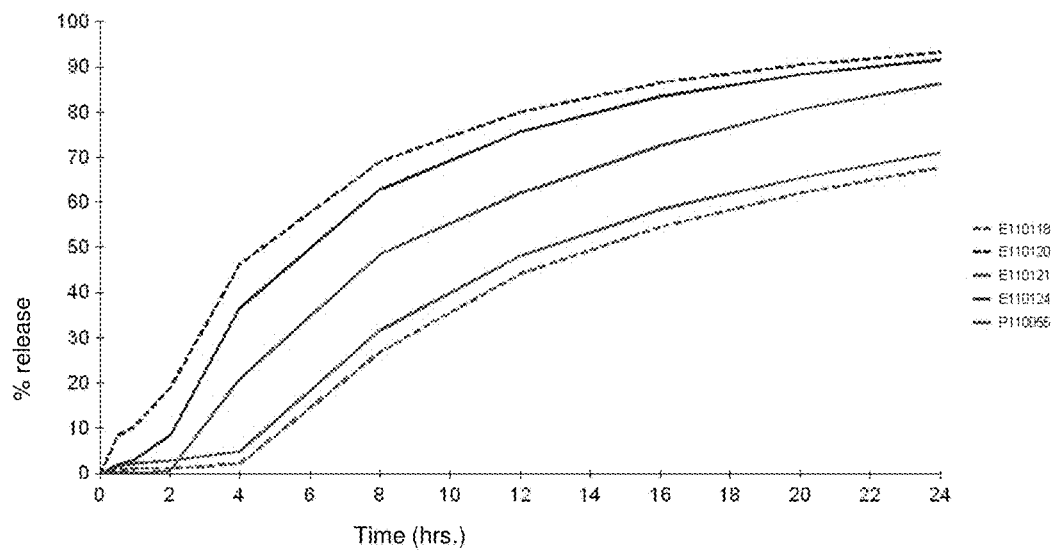
Figure 3: In vitro dissolution profiles

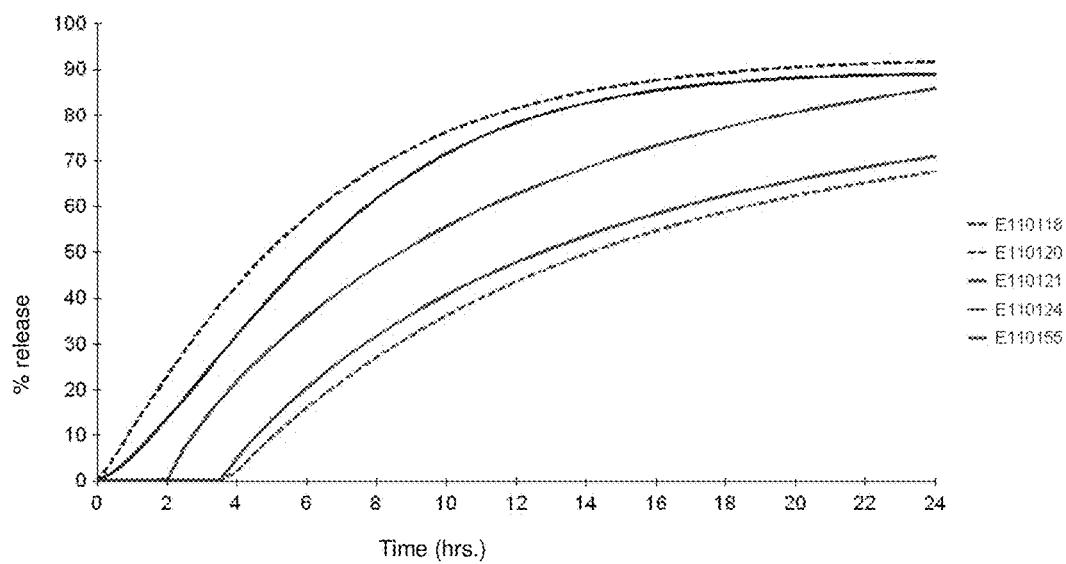
Figure 4: Modelled *in vitro* dissolution profiles
≈ profiles of fractions absorbed *in vivo*

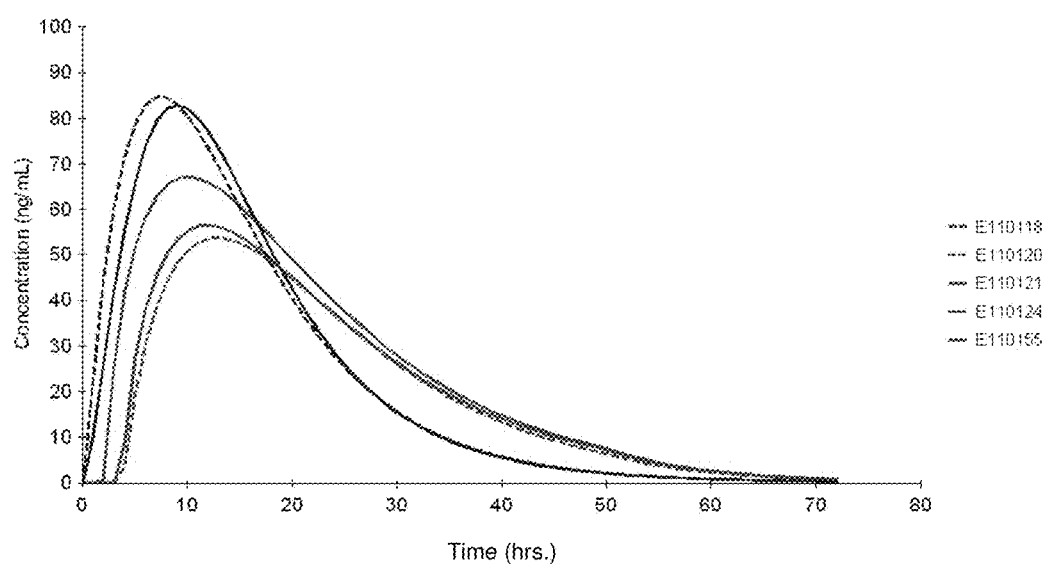
Figure 5: Predicted plasma concentrations obtained by convolution

PHARMACEUTICAL COMPOSITION FOR THE PROLONGED RELEASE OF TRIMETAZIDINE

The invention relates to a pharmaceutical form for the prolonged release of trimetazidine and also to the use thereof in the treatment of angina.

Trimetazidine, or 1-(2,3,4-trimethoxybenzyl)piperazine, is a compound which, by maintaining the energy metabolism of a cell exposed to hypoxia or ischaemia, avoids the collapse of the intracellular level of adenosine triphosphate (ATP). It accordingly ensures functioning of the ion pumps and sodium-potassium trans-membrane flows and maintains cellular homeostasis.

Trimetazidine dihydrochloride is used therapeutically in the prophylactic treatment of angina pectoris attacks, in the course of chorioretinal disorders, and also for the treatment of vertigo of vascular origin (Meniere's vertigo, tinnitus).

The use of trimetazidine therapeutically has been described, in the form of an immediate-release pharmaceutical composition administered three times per day, especially in the patent specification FR 2 490 963.

The patent specification EP 1 108 424 describes a prolonged-release form which makes it possible to cover the entire 24-hour period on the basis of administration twice per day. That prolonged-release form makes it possible to obtain plasma levels in humans which are greater than 70 µg/l after each administration and to maintain a plasma level which is greater than or equal to 40 µg/l before the subsequent administration.

Reservoir-type pharmaceutical compositions for the prolonged release of trimetazidine which ensure release of the active ingredient over a period of 16 hours have been described in the patent specification EP 0 673 649. These reservoir-type forms for single daily administration have the advantage of reducing blood level peaks whilst ensuring regular and constant plasma levels of trimetazidine.

In the therapeutic arsenal available to patients, forms for the prolonged release of trimetazidine are proving necessary in order to ensure compliance and optimum therapeutic protection for the patient. The prolonged-release forms according to the present invention make possible, on the one hand, gradual and sustained release over 24 hours at a therapeutically efficacious plasma concentration of trimetazidine and, on the other hand, the availability of trimetazidine at a therapeutically efficacious plasma concentration a short time after administration. A therapeutically efficacious plasma concentration of trimetazidine is understood to be a plasma level greater than or equal to 40 µg/l, making possible efficacious myocardial protection. Furthermore, a short time is understood to be a period of less than 4 hours, preferably a period of less than 3 hours.

The pharmaceutical composition according to the invention is applied by oral administration once per day and releases trimetazidine throughout the 24-hour period whilst providing a high level of security with respect to any "burst"-type or discontinuous release.

The pharmaceutical composition according to the present invention is a composition for the prolonged release of trimetazidine in which the inner phase comprises trimetazidine and the outer layer comprises a retardant and anti-agglomerant.

The nature and the thickness of the excipients in the outer layer make it possible to control the release of the trimetazidine active ingredient as a function of time. More particularly, the retardant present in the outer layer, i.e. a retardant for the diffusion of the active ingredient, is involved in the process of prolonged release.

Among the retardants that may be used in the compositions according to the invention there may be mentioned, by way of non-limiting example, ethylcellulose (EC), ethylcellulose derivatives such as cellulose acetate, cellulose acetate butyrate, cellulose acetate propionate, cellulose acetate phthalate, hydroxypropyl methylcellulose acetate succinate and/or polymethacrylates. The retardants are placed in organic solution or in aqueous suspension in the course of their being used in the process for manufacture of the pharmaceutical compositions according to the invention. Among the retardants there may be mentioned, more especially, ethylcellulose.

Among the anti-agglomerants according to the invention there may be mentioned talc, silicas and derivatives thereof, magnesium stearate, stearic acid and/or sodium fumaryl stearate. Preference is given to the anti-agglomerant being talc.

Besides the retardant and the anti-agglomerant, the outer layer of the pharmaceutical composition according to the invention comprises a plasticiser. Among the plasticisers which come into consideration according to the invention there may be mentioned acetyl tributyl citrate, glycerol triacetate, acetyl triethyl citrate, acetyl ethyl citrate, diethyl sebacate, dibutyl sebacate, ethyl phthalate, dibutyl phthalate, polyethylene glycol (PEG), glycerol and/or propylene glycol. Among the plasticisers there may be mentioned, more especially, acetyl tributyl citrate.

The percentage of retardant in the pharmaceutical composition is strictly less than 9% of the total weight of the inner phase. More especially, the percentage of retardant is between 5.5% and 8% inclusive of the total weight of the inner phase. The percentage of ethylcellulose in the pharmaceutical composition is strictly less than 9% of the total weight of the inner phase. More especially, the percentage of ethylcellulose is between 5.5% and 8% inclusive of the total weight of the inner phase. More particularly, the percentage of ethylcellulose is 6.5% of the total weight of the inner phase.

The percentage of anti-agglomerant in the pharmaceutical composition is between 25% and 200% inclusive, preferably between 100% and 200% inclusive, of the weight of the retardant.

The percentage of talc as anti-agglomerant in the pharmaceutical composition is preferably between 100% and 200% inclusive of the weight of the retardant.

The percentage of plasticiser in the pharmaceutical composition is between 5% and 50% inclusive, preferably between 5% and 30% inclusive, of the weight of the retardant.

The percentage of acetyl tributyl citrate as plasticiser in the pharmaceutical composition is preferably between 5% and 30% inclusive of the weight of the retardant.

The inner phase of the pharmaceutical compositions according to the present invention comprises the active ingredient trimetazidine and a binder. Among the binders according to the invention there may be mentioned hydroxypropyl methylcellulose (HPMC), hydroxypropylcellulose (HPC), maltodextrin, polyvinylpyrrolidone (PVP) and/or microcrystalline cellulose.

Among the binders there may be mentioned, more especially, hydroxypropyl methylcellulose, which is customarily used in the field of the formulation of medicaments. More especially, the selected hydroxypropyl methylcellulose is of low viscosity. Preferably, the hydroxypropyl methylcellulose used is Pharmacoat™ 606.

Preferably, the trimetazidine and the binder are deposited on a neutral core, the entirety thereof constituting the inner phase.

The cores or pellets used may be soluble or insoluble in water. These cores are spheres of sugar or spheres of sucrose/starch or of microcrystalline cellulose, smoothed and protected—or not—by a pharmaceutical excipient, preferably by cellulose derivatives. The size of the cores varies from 100 to 1200 μm, preferably from 300 to 1000 μm and, even more preferably, from 710 to 850 μm; where appropriate, the size may be modified if it proves necessary.

Preference is given to the trimetazidine in the compositions according to the invention being in the form of the dihydrochloride of trimetazidine. The amount of trimetazidine dihydrochloride in the pharmaceutical composition is preferably 80 mg.

The percentage of binders in the pharmaceutical composition is between 1% and 15% inclusive of the total weight of the composition. The percentage of hydroxypropyl methylcellulose as binder in the pharmaceutical composition is between 1% and 15% inclusive of the total weight of the composition.

The percentage of neutral cores in the pharmaceutical composition is between 15% and 40% inclusive of the total weight of the composition. The percentage of cores of the sucrose/starch type is between 15% and 40% inclusive of the total weight of the composition.

The percentage of trimetazidine in the pharmaceutical composition is between 35% and 70% of the total weight of the composition.

Preferably, the outer layer of the pharmaceutical compositions according to the invention comprises from 5.5% to 8% of ethylcellulose relative to the total weight of the inner phase, from 5% to 30% of acetyl tributyl citrate relative to the weight of the retardant and from 100% to 200% of talc relative to the weight of the retardant.

Likewise preferably, the inner phase of the pharmaceutical compositions according to the invention comprises from 15% to 40% of neutral core, from 35% to 70% of trimetazidine and from 1% to 15% of hydroxypropyl methylcellulose relative to the total weight of the composition.

The amount of components of the pharmaceutical composition is 80 mg of trimetazidine dihydrochloride, 36.677 mg of neutral minigranules, 6.40 mg of hydroxypropyl methylcellulose, 1.2 mg of acetyl tributyl citrate, 8 mg of ethylcellulose and 12 mg of talc.

Among the pharmaceutical compositions according to the invention there may be mentioned, more especially, those that are suitable for oral administration, especially in capsule form.

The in vitro dissolution rate of the composition according to the invention, obtained according to the methodology of the European Pharmacopoeia, is from 8% to 28% of the trimetazidine released by 4 hours and from 37% to 57% of the trimetazidine released by 8 hours and more than 75% of the trimetazidine released by 24 hours. These dissolution kinetics are selected so that the therapeutically efficacious plasma concentration of trimetazidine obtained in vivo is prolonged over 24 hours following administration of the pharmaceutical composition.

In accordance with the process for manufacture of the pharmaceutical compositions according to the invention, cores are coated with successive layers of the active ingredient using a coating pan, with or without perforations, or fluidised-bed apparatus. The active ingredient in the form of a solution or suspension, which is aqueous or organic, is sprayed onto the cores and then dried.

The minigranules, prepared by one or other of the processes, are subsequently coated, either in a coating pan, with or without perforations, or in a fluidised-bed type apparatus. The minigranules are coated using a solution or suspension of the retardant which is involved in the diffusion of the active ingredient and thereby controls the release kinetics.

The coated minigranules are placed in capsules.

By way of example, the following manufacturing process may be mentioned:

Neutral cores composed of sucrose/starch are coated with successive layers of trimetazidine hydrochloride solution associated with hydroxypropyl methylcellulose in a fluidised-bed system.

Coating of the minigranules thereby prepared is carried out in a fluidised-bed apparatus using a suspension composed of ethylcellulose, acetyl tributyl citrate and talc.

The coated minigranules are filled into capsules in the presence of magnesium stearate.

The present invention relates also to use of the pharmaceutical compositions according to the invention in the prophylactic treatment of angina pectoris, in the course of chorioretinal disorders and also for the treatment of vertigo of vascular origin.

BRIEF DESCRIPTION OF THE DRAWINGS

FIG. 1 shows the structure and formulation of the pharmaceutical composition described in Table 1.

FIG. 2 shows the comparative appearance of minigranules without anti-agglomerant (top) and with an excess of anti-agglomerant (bottom).

FIG. 3 shows the in vitro dissolution profiles of the pharmaceutical compositions described in Example 3.

FIG. 4 shows the modelled in vitro dissolution profiles for the pharmaceutical compositions described in Example 3.

FIG. 5 shows the predicted mean pharmacokinetic profiles for the pharmaceutical compositions described in Example 3.

The Examples hereinbelow illustrate, but do not limit, the invention.

EXAMPLE 1: PHARMACEUTICAL COMPOSITION FOR A CAPSULE CONTAINING 80 MG OF TRIMETAZIDINE

The trimetazidine minigranules are coated with a film containing 6.5% ethylcellulose.

FIG. 1 illustrates the structure and formulation of the pharmaceutical composition described below.

TABLE 1

| Compounds | Amount (mg) |
| --- | --- |
| Active ingredient minigranules | |
| Trimetazidine dihydrochloride | 80.00 |
| Neutral minigranules | 36.677 |
| Hydroxypropyl methylcellulose | 6.40 |
| Coating (6.5% EC) | |
| Acetyl tributyl citrate | 1.20 |
| Ethylcellulose | 8.00 |
| Talc | 12.00 |

TABLE 1-continued

| Compounds | Amount (mg) |
|---|---|
| Capsule | |
| Coated minigranules | 144.277 |
| Magnesium stearate | 0.434 |

EXAMPLE 2: MACROSCOPIC APPEARANCE OF THE MINIGRANULES

In the absence of anti-agglomerant in the outer phase of the pharmaceutical compositions there are found, on an industrial scale, irregular minigranules (FIG. 2), numerous cracks in the minigranules' coating and even amalgamations between the minigranules. These coating defects cause major modifications to the in vitro dissolution kinetics, especially profiles of accelerated dissolution.

If the anti-agglomerant is in excess, then the minigranules obtained on an industrial scale have an irregular and flaky surface (FIG. 2) due to the presence of excessive talc sticking to the surface of the minigranules. These minigranules have dissolution kinetics that are greatly accelerated and even immediate-release kinetics.

EXAMPLE 3: DISSOLUTION KINETICS COMPARED AS A FUNCTION OF THE PERCENTAGE OF ETHYLCELLULOSE IN THE COATING

TABLE 2

| Batch | E110055 | E110118 | E110120 | E110121 | E110124 |
|---|---|---|---|---|---|
| EC % | 6.5 | 10 | 4.5 | 9 | 5 |
| Coating ratio % | 14.7 | 20.9 | 10.7 | 19.3 | 11.7 |
| Composition | | | | | |
| Tri-metazidine | 80 | 80 | 80 | 80 | 80 |
| Neutral cores | 36.677 | 36.677 | 36.677 | 36.677 | 36.677 |
| HMPC | 6.4 | 6.4 | 6.4 | 6.4 | 6.4 |
| Ethyl-cellulose | 8 | 12.3 | 5.5 | 11.1 | 6.2 |
| Acetyl tributyl citrate | 1.2 | 1.8 | 0.8 | 1.7 | 0.9 |
| Talc | 12 | 18.5 | 8.3 | 16.7 | 9.3 |
| Mg stearate | 0.4 | 0.4 | 0.4 | 0.4 | 0.4 |
| Total weight | 144.711 | 156 | 138 | 152.9 | 139.8 |
| Dissolution | | | | | |
| 4 hrs | 20.9 | 2.1 | 46.3 | 4.9 | 36.6 |
| 8 hrs | 48.5 | 26.9 | 69.1 | 31.7 | 62.9 |
| 12 hrs | 62.0 | 44.1 | 80 | 48.1 | 75.7 |
| 16 hrs | 72.6 | 54.5 | 86.5 | 58.3 | 83.4 |
| 24 hrs | 86.3 | 67.8 | 93.2 | 71.1 | 91.6 |

It is to be noted that the coating ratio was calculated as follows: weight of outer phase/total weight.

Furthermore, the above dissolution profiles were obtained starting from minigranules which had not been distributed into capsules. The dissolution profiles of batches on an industrial scale (minigranules encapsulated in capsules) are slowed down by 4, 3, 2 and 1% at the 4, 8, 12 and 16 hour points, respectively, relative to the dissolution profiles described above (not filled).

The in vitro dissolution kinetics of the pharmaceutical compositions E110118 (EC 10%), E110120 (EC 4.5%), E110121 (EC 9%), and E110124 (EC 5%) (FIG. 4) were compared to the in vitro release kinetics of the reference pharmaceutical composition E110055 (EC 6.5%). The dissolution profiles are compared with the aid of the similarity factor ($f_2$).

The dissolution kinetics of the compositions E110118 (EC 10%) and E110121 (EC 9%), on the one hand, and E110120 (EC 4.5%) and E110124 (EC 5%), on the other hand, are not similar to the dissolution kinetics of the reference pharmaceutical composition E110055 (EC 6.5%). Consequently, the percentage of retardant in the pharmaceutical composition is, on the one hand, strictly less than 9% and, on the other hand, strictly greater than 5%.

Two dissolution profiles are considered to be similar when the value ($f_2$) is greater than or equal to 50. Calculation of the similarity factor ($f_2$) is advised by the directives of the EMA and the FDA in order to compare two dissolution profiles and to make it possible to decide if said dissolution profiles are the same.

The similarity factor ($f_2$) has the following formula:

$$f_2 = 50 \cdot \log \{[1+(1/n)\Sigma_{t=1}^{n}(R_{(t)}-T_{(t)})^2]^{-0.5} \cdot 100\}$$

wherein $f_2$ is the similarity factor, n is the number of normalised points, R(t) is the percentage mean of active ingredient dissolved from the reference pharmaceutical composition E110055 and T(t) is the percentage mean of active ingredient dissolved from a pharmaceutical composition E110118 (EC 10%), E110120 (EC 4.5%), E110121 (EC 9%), and E110124 (EC 5%). The normalised points are at least at t=8 hours, t=12 hours and t=16 hours.

The evaluated minigranules filled into capsules have different formulations; these formulations vary especially as a function of the amount of ethylcellulose and anti-agglomerant.

The observed in vitro dissolution profiles of the pharmaceutical compositions E110118 (EC 10%), E110120 (EC 4.5%), E110121 (EC 9%), and E110124 (EC 5%) (FIG. 3) were modelled by applying Weibull's law to each of them (FIG. 4). Weibull's law constitutes an especially valuable approximation which makes it possible to predict continuous in vitro dissolution profiles from observed in vitro dissolution profiles.

A vitro-vivo correlation equal to 1 was put forward as the hypothesis; consequently the profiles of the fractions absorbed in vivo (FIG. 4) correspond exactly to the modelled in vitro dissolution profiles. A convolution step was then carried out in order to predict the pharmacokinetic profiles of the various pharmaceutical compositions. The convolution step (function Cp(t)) is defined as follows:

$$Cp(t) = I(t) * P(t)$$

wherein I(t) is an input function and P(t) is a disposition function.

The input function represents the fractions absorbed in vivo as a function of time and the disposition function is a polyexponential equation of the pharmacokinetics of a pharmaceutical composition for the prolonged release of trimetazidine obtained in the study SKH-6790-005-FRA. The predicted mean pharmacokinetic profiles are shown in FIG. 5.

Starting from said plasma profiles obtained by convolution, the pharmacokinetic parameters AUC and Cmax were calculated where AUC represents the exposure to the medicament and Cmax the maximum concentration.

TABLE 3

|  | AUC (ng · h/mL) | Cmax (ng/mL) |
|---|---|---|
| E110124 | 1620 | 83.6 |
| E110120 | 1678 | 85.6 |
| E110055 | 1776 | 67.8 |
| E110121 | 1501 | 57.0 |
| E110118 | 1418 | 54.2 |

The AUC of the pharmaceutical composition E110055 (EC 6.5%) is the highest of the pharmaceutical compositions evaluated above and the exposure of the patient to the trimetazidine is significantly improved.

Furthermore, the pharmacokinetic profiles make it possible to measure the efficacious myocardial protection time of the treated patient, or the time during which said patient is covered by a therapeutically efficacious plasma concentration (40 μg/l). This therapeutic protection time is at least 22 hours for the composition E110155 (EC 6.5%) whereas it is only 16 hours for the composition E110118 (EC 10%). The therapeutic protection time is improved even when the percentage of retardant, which is responsible for the prolonged release in the therapeutic composition, is reduced from 10% to 6.5%.

The invention claimed is:

1. A pharmaceutical composition for prolonged release of trimetazidine, comprising:
    an inner phase which comprises trimetazidine, or a pharmaceutically acceptable salt thereof, coated onto a neutral core; and
    an outer layer consisting of a retardant, an anti-agglomerant, and a plasticiser,
wherein the percentage of retardant is from 5.5% to 8% of the total weight of the inner phase; and the percentage of anti-agglomerant is from 100% to 200% of the weight of the retardant.

2. The composition according to claim 1, wherein the retardant is selected from the group consisting of ethylcellulose, cellulose acetate, cellulose acetate butyrate, cellulose acetate propionate, cellulose acetate phthalate, hydroxypropyl methylcellulose acetate succinate and polymethacrylates.

3. The composition according to claim 1, wherein the anti-agglomerant is selected from the group consisting of talc, colloidal silicon dioxide, magnesium stearate, stearic acid and sodium fumaryl stearate.

4. The composition according to claim 1, wherein the plasticiser is selected from the group consisting of acetyl tributyl citrate, glycerol triacetate, acetyl triethyl citrate, acetyl ethyl citrate, diethyl sebacate, dibutyl sebacate, ethyl and dibutyl phthalate, polyethylene glycol, glycerol and propylene glycol.

5. The composition according to claim 1, wherein the percentage of plasticiser is between 5% and 50% inclusive of the weight of the retardant.

6. The composition according to claim 1, wherein the inner phase further comprises a binder.

7. The composition according to claim 6, wherein the binder is selected from the group consisting of hydroxypropyl methylcellulose, hydroxypropylcellulose, maltodextrin, polyvinylpyrrolidone and microcrystalline cellulose.

8. The composition according to claim 6, wherein the binder is hydroxypropyl methylcellulose.

9. The composition according to claim 1, wherein the neutral core comprises sucrose, sucrose and starch, or microcrystalline cellulose.

10. The composition according to claim 1, wherein the trimetazidine is in the form of the dihydrochloride.

11. The composition according to claim 1, wherein the composition contains 80 mg of trimetazidine dihydrochloride as the pharmaceutically acceptable salt of trimetazidine.

12. The composition according to claim 1, wherein the retardant is ethylcellulose; the anti-agglomerant is talc; and the plasticiser is acetyl tributyl citrate and wherein:
    the acetyl tributyl citrate is present in an amount of from 5% to 30% relative to the weight of the retardant;
    the ethylcellulose is present in an amount of from 5.5% to 8% relative to the total weight of the inner phase; and
    the talc is present in an amount from 100% to 200% relative to the weight of the retardant.

13. The composition according to claim 8, wherein the inner phase comprises:
    from 15% to 40% of neutral core relative to the total weight of the composition;
    from 35% to 70% of trimetazidine relative to the total weight of the composition;
    from 1% to 15% of hydroxypropyl methylcellulose relative to the total weight of the composition.

14. The composition according to claim 13, wherein the neutral core comprises minigranules, and wherein the outer layer consists of ethylcellulose as the retardant, talc as the anti-agglomerant, and acetyl tributyl citrate as the plasticiser.

15. The composition according to claim 1, wherein the level of in vitro dissolution of the composition is from 8% to 28% of the trimetazidine released by 4 hours and from 37% to 57% of the trimetazidine released by 8 hours and more than 75% of the trimetazidine released by 24 hours and is selected so that the therapeutically efficacious plasma concentration of trimetazidine obtained in vivo is prolonged over 24 hours following administration of the composition.

16. The composition according to claim 14, wherein the neutral core comprises 80 mg of trimetazidine dihydrochloride, as the pharmaceutically acceptable salt of trimetazidine, 36.677 mg of neutral minigranules, and 6.40 mg of hydroxypropyl methylcellulose, and the outer layer consists of 1.2 mg of acetyl tributyl citrate, 8 mg of ethylcellulose, and 12 mg of talc.

* * * * *